United States Patent
Gauvry et al.

(10) Patent No.: US 10,370,375 B2
(45) Date of Patent: *Aug. 6, 2019

(54) HETEROCYCLYL-SUBSTITUTED CYCLOHEXYLSULFONAMIDES AS JAK INHIBITORS

(71) Applicant: Elanco Tiergesundheit AG, Indianapolis, IN (US)

(72) Inventors: Noelle Gauvry, Kembs (FR); Chouaib Tahtaoui, Rixheim (FR); Pascal Furet, Thann (FR); Pierre Ducray, Village-Neuf (FR)

(73) Assignee: Elanco Tiergesundheit AG, Greenfield, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/055,560

(22) Filed: Aug. 6, 2018

(65) Prior Publication Data
US 2018/0346465 A1 Dec. 6, 2018

Related U.S. Application Data

(63) Continuation of application No. 15/119,800, filed as application No. PCT/EP2015/056430 on Mar. 25, 2015, now Pat. No. 10,059,709.

(30) Foreign Application Priority Data

Mar. 28, 2014 (EP) .................... 14162391

(51) Int. Cl.
| C07D 471/14 | (2006.01) |
| C07D 239/46 | (2006.01) |
| C07D 471/04 | (2006.01) |
| C07D 473/34 | (2006.01) |
| C07D 487/04 | (2006.01) |
| C07D 495/04 | (2006.01) |
| C07D 239/42 | (2006.01) |
| C07D 239/48 | (2006.01) |

(52) U.S. Cl.
CPC ......... *C07D 471/14* (2013.01); *C07D 239/42* (2013.01); *C07D 239/46* (2013.01); *C07D 239/48* (2013.01); *C07D 471/04* (2013.01); *C07D 473/34* (2013.01); *C07D 487/04* (2013.01); *C07D 495/04* (2013.01)

(58) Field of Classification Search
CPC ... C07D 471/14; C07D 239/42; C07D 471/04

USPC ....................................................... 514/243
See application file for complete search history.

(56) References Cited

U.S. PATENT DOCUMENTS

| 8,461,328 B2 * | 6/2013 | Babu ................ C07D 487/10 540/597 |
| 10,059,709 B2 * | 8/2018 | Gauvry .............. C07D 471/14 |
| 2009/0264399 A1 | 10/2009 | Inoue et al. |
| 2011/0201593 A1 | 8/2011 | Babu et al. |

FOREIGN PATENT DOCUMENTS

| WO | 2006/069080 A2 | 6/2006 |
| WO | 2006/127587 A1 | 11/2006 |
| WO | 2010/002472 A1 | 1/2010 |
| WO | 2010/020905 A1 | 2/2010 |
| WO | 2011/014817 A1 | 2/2011 |
| WO | 2011/045702 A1 | 4/2011 |
| WO | 2011/075344 A1 | 6/2011 |
| WO | 2011/086053 A1 | 7/2011 |
| WO | 2012/030894 A1 | 3/2012 |
| WO | 2013/007765 A1 | 1/2013 |
| WO | 2013/024895 A1 | 2/2013 |

OTHER PUBLICATIONS

Mark Zak, 2012, Discovery and Optimization of C-2 Methyl Imisapyrrolopyridines as Potent and Orally Bioavailable JAK1 Inhibitors with Selectivity over JAK2.

* cited by examiner

*Primary Examiner* — Rita J Desai
(74) *Attorney, Agent, or Firm* — Joseph Matthew Pletcher

(57) ABSTRACT

The invention relates to a compound of formula (I) wherein the variables have the meaning as indicated in the claims; in free form and in salt form; and optionally the enantiomers and geometrical isomers thereof. The compounds of formula (I) are useful as therapeutic agent for organ transplants, lupus, multiple sclerosis, rheumatoid arthritis, psoriasis. Type I diabetes and complications from diabetes, cancer, asthma, atopic dermatitis, autoimmune thyroid disorders, ulcerative colitis, inflammatory bowel diseases, Crohn's disease, Alzheimer's disease, leukemia, osteoarthritis, control of pruritus, chronic respiratory disease or keratoconjunctivitis in mammals.

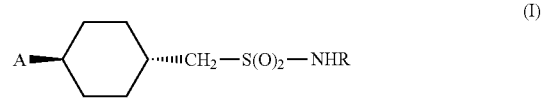

(I)

5 Claims, No Drawings

HETEROCYCLYL-SUBSTITUTED CYCLOHEXYLSULFONAMIDES AS JAK INHIBITORS

The present invention relates to novel heterocyclyl-substituted cyclohexylmethansulfonamides which are Janus kinase inhibitors, also known as JAK inhibitors, and their use in the treatment of allergic reactions including allergic dermatitis, eczema, atopic dermatitis, pruritus and other pruritic conditions and also inflammatory diseases.

Oclacitinib, a pyrrolopyrimidinaminocyctohexylmethansulfonamide, is a JAK inhibitor, which is approved for the control of pruritus associated with allergic dermatitis and the control of atopic dermatitis in dogs. However, the search for new, more potent JAK inhibitor molecules continues. Surprisingly, new specific JAK inhibitors have been found which provide an improved activity concerning skin diseases, in particular atopic dermatitis and pruritus.

The present invention therefore in one aspect concerns a compound of formula

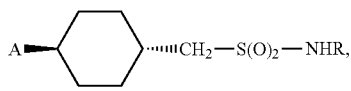
(1)

wherein R is $C_1$-$C_4$-alkyl or $C_3$-$C_5$-cycloalkyl; and A is
(i) a radical of formula

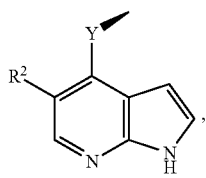
(2a)

wherein either Y is NH, N($C_1$-$C_2$-alkyl) or O, $R^2$ is cyano (CN), nitro ($NO_2$) C(O)NR'R", C(O)OR' or NR'R", and R' and R" are each independently of the other H or $C_1$-$C_4$-alkyl; or
Y and $R^2$ together form a bivalent radical

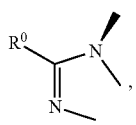

wherein $R^0$ is H, $C_1$-$C_4$-alkyl, hydroxy-$C_1$-$C_4$-alkyl, $C_1$-$C_4$-alkoxy-$C_1$-$C_4$-alkyl or $NH_2$ and preferably H, $C_1$-$C_4$-alkyl or $NH_2$;
or is (ii) a radical of formula

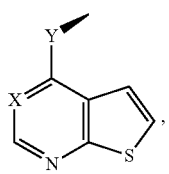
(2b)

wherein X is N, C(CN), C($NO_2$), C[C(O)NR'R"], C[C(O)OR'] or C(NR'R"), and Y, R' and R" are as defined above;
or is (iii) a radical of formula

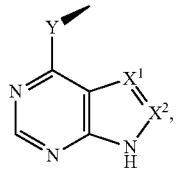
(2c)

wherein one of $X^1$ and $X^2$ is N and the other one is C($R^3$), $R^3$ is H, $C_1$-$C_4$-alkyl, phenyl or benzyl, and Y is as defined above;
or is (iv) a radical of formula

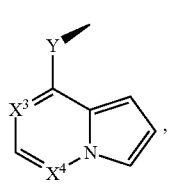
(2d)

wherein either $X^3$ is N and $X^4$ is CH or N, or $X^1$ is C(CN), C($NO_2$), C[C(O)NR'R"], C[C(O)OR'] or C(NR'R") and $X^4$ is N, and wherein Y. R' and R" are as defined above;
or is (v) a radical of formula

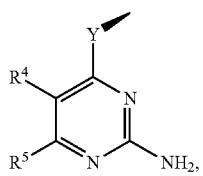
(2e)

wherein $R^4$ and $R^5$ are each independently of the other H, halogen, $C_1$-$C_4$-alkyl or phenyl, and Y is as defined above.

The variable R is preferably methyl, ethyl or cyclobutyl, in particular methyl.

$R^0$ as hydroxyl-$C_1$-$C_4$-alkyl is preferably hydroxymethyl or hydroxyethyl, in particular hydroxymethyl. $R^0$ as $C_1$-$C_4$-alkoxy-$C_1$-$C_4$-alkyl is preferably methoxymethyl or ethoxymethyl, in particular methoxymethyl. The variable $R^0$ is preferably H, methyl hydroxymethyl, methoxymethyl or $NH_2$, more preferably H, methyl or $NH_2$, in particular H. R' and R" are each independently of the other preferred H, methyl or ethyl. $R^2$ is preferably cyano or nitro.

One embodiment of the invention concerns a radical A of formula (2a), wherein $R^2$ and Y have the meanings as defined. A preferred radical A is of formula (2a), wherein $R^2$ is cyano or nitro and Y is NH, N($CH_3$) or O, preferably NH or N($CH_3$), in particular N($CH_3$).

Still a further preferred radical A is a radical of formula

(2a')

Preferred radicals of formula (2b) are a radical

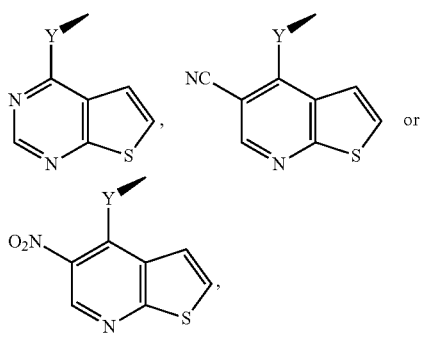

wherein Y is in each case O, NH or N(CH$_3$), in particular N(CH$_3$), or O, in particular N(CH$_3$).

A further embodiment of the invention concerns a radical A of formula (2c), wherein X$^1$ is CH and X$^2$ is N. Still a further embodiment concerns a radical A of formula (2c) wherein X$^1$ is N, X$^2$ is C(R$^3$) and R$^3$ is H, C$_1$-C$_4$-alkyl, phenyl or benzyl, preferably H, methyl, phenyl or benzyl.

Preferred radicals of formula (2d) are:

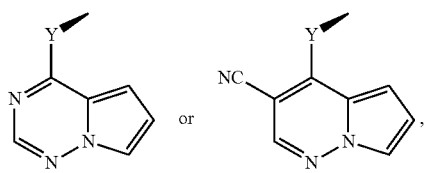

wherein Y is in each case NH or N(CH$_3$).

A further embodiment concerns a radical A of formula (2e), wherein one of R$^4$ and R$^5$ is H and the other one is H, halogen, or phenyl and Y is NH or N(CH$_3$).

The compounds of this invention can exist as one or more stereoisomers. The various stereoisomers include enantiomers, diastereomers, atropisomers and geometric isomers.

In case the compounds of the formula (I) have a chiral carbon atom, they may have either an (R) or an (S) configuration. The present invention encompasses compounds formula (I) both with (S) and with (R) configuration at the particular chiral carbon atoms, which means that the present invention covers the compounds of the general formula (I) in which the carbon atoms in question each independently have an (R) configuration; or have an (S) configuration.

If a plurality of chiral centres are present in the compounds of the formula (I) any desired combinations of the configurations of the chiral centres are possible, which means that (1) one chiral centre may have (R) configuration and the other chiral centre (S) configuration; (2) one chiral centre may have (R) configuration and the other chiral centre (R) configuration; and (3) one chiral centre may have (S) configuration and the other chiral centre (S) configuration.

One skilled in the art will appreciate that one stereoisomer may be more active and/or may exhibit beneficial effects when enriched relative to the other stereoisomers) or when separated from the other stereoisomers). Additionally, the skilled artisan knows how to separate, enrich, and/or to selectively prepare said stereoisomers. The compounds of the invention may be present as a mixture of stereoisomers, individual stereoisomers, or as an optically active form.

One skilled in the art will appreciate that not all nitrogen containing heterocyclic rings can form N-oxides since the nitrogen requires an available lone pair for oxidation to the oxide; one skilled in the art will recognize those nitrogen containing heterocyclic rings which can form N-oxides. One skilled in the art will also recognize that tertiary amines can form N-oxides. Synthetic methods for the preparation of N-oxides of heterocyclic rings and tertiary amines are very well known by one skilled in the art including the oxidation of heterocyclic rings and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyl dioxirane These methods for the preparation of N-oxides have been extensively described and reviewed in the literature. The manufacture of suitable S-oxides may be performed in an analogous manner using, for example, the same kind of oxidants as mentioned above for the N-oxides.

One skilled m the art recognizes that because of the environment and under physiological conditions salts of chemical compounds are in equilibrium with their corresponding nonsalt forms, salts share the biological utility of the nonsalt forms. Thus a wide variety of salts of the compounds of formula (I) are useful (i.e. are veterinarily suitable). The salts of the compounds of formula (I) include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic "or valeric acids. When a compound of formula (I) contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from formula (I), N-oxides and veterinary acceptable salts thereof. The compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. Exemplary prodrugs are, e.g., esters of free carboxylic acids and S-acyl and O-acyl derivatives of thiols, alcohols or phenols, wherein acyl has a meaning as defined herein. Preferred are veterinary or pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the -(amino, mono- or di-lower alkylamino, carboxy, lower alkoxycarbonyl)-lower alkyl esters, the -(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde. Moreover, drugs containing an acidic NH group, such as imidazole, imide, indole and the like, have been masked with N-acyloxy-methyl groups. Hydroxy groups have been masked as esters and ethers. EP0 039 051 discloses Mannich-base hydroxamic acid prodrugs, their preparation and use. In view of the close relationship between the compounds, the compounds in the form of their salts and the pro-drugs, any reference to the compounds of the present invention is to be understood as referring also to the corresponding pro-drugs of the compounds of the present invention, as appropriate and expedient.

The compounds of formula (I) may be prepared, for example, by reacting a compound of Formula A'-Hal  (3)

with
a compound of formula

  (4)

wherein Y and R are as defined above, Hal is halogen, for example, chlorine, and A' is a radical of formula

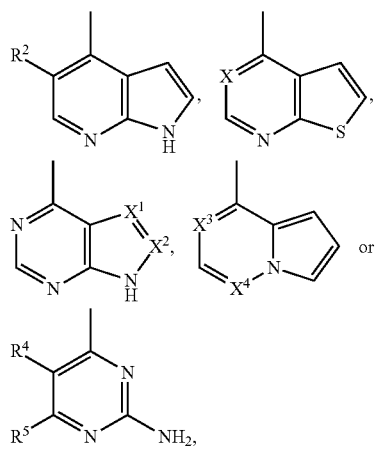

wherein $R^2$, $R^4$, $R^5$, $X^1$, $X^2$, $X^3$ and $X^4$ are as defined above. The nucleophilic substitution reaction may be performed, for example, as described in textbooks of organic chemistry. For example, the compounds of formula (3) and (4) are reacted in a suitable solvent or mixture of solvents in the presence of a base. The choice of solvent and base is strongly dependent on the specific nature of the compounds of formulae (3) and (4). The reaction may take place at room temperature or at elevated temperature, for example, above 100° C. In case of a compound of formula (3) comprising a radical A' with a NH group, it may be advisable to protect said amine group before performing the reaction with the compound of formula (4). The protection of the amine group and deprotection afterwards may be performed in a manner known per se.

Alternatively the compounds of formula (3) and (4) can be coupled via the Buchwald-Hartwig Pd catalyzed amination as described in textbooks of organic chemistry.

The compounds of formula (3) are known per se or may be prepared according to methods known per sc.

The compounds of formula (4) are likewise known, or may be prepared according to methods known per sc. For example, the HY-group of a compound of formula

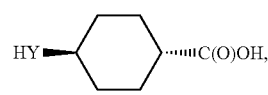  (5)

wherein Y is as defined above, is first protected in a manner known per se, before reducing the carboxyl group to yield the corresponding alcohol of formula

  (6)

wherein PC is a protective group and Y is as defined above. The alcohol of formula (6) is then converted to the corresponding compound of formula (7)

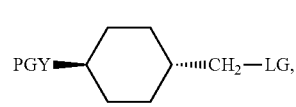  (7)

wherein LG is a leaving group, for example, chlorine, bromine, mesylate or tosylate, which is in turn converted to the corresponding sulfonic acid of formula (8)

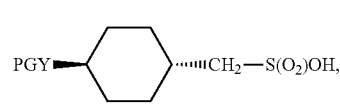  (8)

using sodium sulphite or sodium thioacetate followed by hydrogen peroxide oxidation.

The compound of formula (8), after having been converted to the corresponding methane sulfonic halide, for example by reaction with thionyl chloride, is reacted with an amine of formula

  (9)

wherein R is as defined above, to yield a compound of formula (4) in protected form, which is finally deprotected. The above outlined steps from the compound of formula (5) to the compound of formula (4) are all well-known reactions which may be performed as disclosed in textbooks of organic chemistry. The working examples further illustrate the reactions.

In the alternative, the compounds of formula (1) may be synthesized in analogy to WO2010/020905, Scheme II on page 14.

In addition, a compound of formula (1), wherein A is a radical of formula

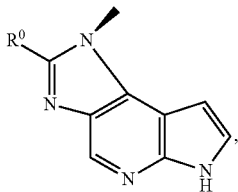

(2a')

wherein R⁰ is as defined above, may be obtained by preparing first of all a compound of formula

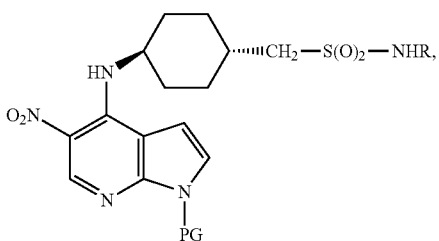

(1a)

wherein PC is a protective group, by a process as described above, reducing the nitro group of the compound of formula (1a) in a manner known per se, for example catalytically with H₂/Rancy Nickel, and reacting the resulting diamine with an acid halide R⁰—C(O)Hal or with a trialkyl ortho-ester (AlkO)₃—C—R⁰, wherein Hal is Br or Cl, Alk is, for example, ethyl and R⁰ is as disclosed above, in order to yield a compound of formula

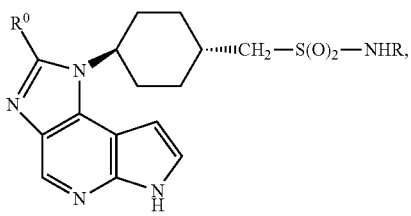

(1b)

after deprotection of the amine, wherein R and R⁰ are as disclosed above.

The compounds of the present invention are Janus Kinase inhibitors (JAK-i) with efficacy, for example, against Janus Kinase-1 (JAK-1), Janus Kinase-2 (JAK-2), Janus Kinase-3 (JAK-3) and Tyrosine Kinase-2 kinase (TYK-2), in particular JAK-1 or JAK-3. Accordingly, they are useful as therapeutic agents for organ transplants, lupus, multiple sclerosis, rheumatoid arthritis, psoriasis, Type 1 diabetes and complications from diabetes, cancer, asthma, atopic dermatitis, autoimmune thyroid disorders, ulcerative colitis, inflammatory bowel diseases, Crohn's disease, Alzheimer's disease, leukemia, osteoarthritis, control of pruritus, chronic respiratory disease, keratoconjunctivitis and other indications where immunosuppression/immunomodulation would be desirable.

In particular it has turned out that the compounds of the present invention are safe and efficacious agents to control skin diseases, conditions or disorders including atopic dermatitis, eczema, psoriasis, scleroderma, pruritus and other pruritic conditions; allergic reactions including allergic dermatitis in mammal including horse allergic diseases such as bite hypersensitivity, summer eczema and sweet itch in horses.

As the compounds of the present invention are JAK inhibitors with efficacy against JAK-1 and JAK-3, they provide resolution of chronic pruritus and inflammation that would either persist in atopic dermatitis or slowly regress following removal of allergen or causative agent, such as fleas in flea-allergic dermatitis.

Compounds of the present invention may be administered in a pharmaceutically acceptable form either alone or in combination with one or more additional agents which modulate a mammalian immune system or with antiinflammatory agents. Examples are cyclosporin A aspirin, acetaminophen, ibuprofen, naproxen, piroxicam, and antiinflammatory steroids (e.g. prednisolone or dexamethasone). These agents may be administered as part of the same or separate dosage forms, via the same or different routes of administration, and on the same or different administration schedules according to standard pharmaceutical practice known to one skilled in the art.

In one embodiment, the invention provides methods of treating or preventing a disease, condition or disorder associated with JAK in a subject, such as a human or non-human mammal, comprising administering an effective amount of one or more compounds described herein to the subject. The JAK associated disease, condition or disorder can be related to JAK-1, JAK-2, JAK-3, and/or TYK-2. Suitable subjects that can be treated include domestic or wild animals, companion animals, such as dogs, cats, horses and the like; livestock including, cows and other ruminants, pigs, poultry, rabbits and the like; primates, for example monkeys, and rodents such as rats mice, gerbils guinea pigs and the like. In one embodiment, the compound is administered in a pharmaceutically acceptable form, optionally in a pharmaceutically acceptable carrier.

Another embodiment provides a method of inhibiting a JAK enzyme, including JAK-1, JAK-2, JAK-3 and/or Tyk-2, that includes contacting the JAK enzyme with either a non-therapeutic amount or a therapeutically effective amount of one or more of the present compounds. Such methods can occur in vivo or in vitro. In vitro contact can involve a screening assay to determine the efficacy of the one or more compounds against a selected enzyme at various amounts or concentrations. In vivo contact with a therapeutically effective amount of the one or more compounds can involve treatment of a described disease, disorder or condition or prophylaxis of organ transplant rejection in the animal in which the contact occurs. The effect of the one or more compounds on the JAK enzyme and/or host animal can also be determined or measured. Methods for determining JAK activity are shown in the Examples part below.

In therapeutic use for treating disorders in a mammal (i.e. human and animals), a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying. Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention.

The formulations of the invention can be designed to be short-acting, fast-releasing, long-acting, and sustained-releasing. Thus, the pharmaceutical formulations can also be formulated for controlled release or for slow release.

Pharmaceutical compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day. It is to be understood that the dosages may vary depending upon the requirements of each subject and the severity of the disorders or diseases being treated. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

The Examples further illustrate the invention.

EXAMPLE 1

This example illustrates the preparation of 1-[trans-4-(imidazo[4,5-d]pyrrolo[2,3-b]pyridin-1(6H)-yl)cyclohexyl]-N-methylmethanesulfonamide (Compound 22 in Table 1)

Step A methyl trans-4-aminocyclohexanecarboxylate (0.19 g), acetonitrile (3 ml) and $K_2CO_3$ (0.407 g) were placed in a round bottomed flask with magnetic agitator and heating bath. Benzyl bromide (0.29 ml) was added and reaction mixture was vigorously agitated at 25 to 30° C. for 3 hours. TLC (DCM/MeOH 8:1) revealed foil conversion of starting material and monobenzylated amine presence. Inorganic precipitate was filtered off. Filtrate was evaporated. The residue was purified by chromatography on silica gel (DCM/Hexane 1:1 to DCM/MeOH 10:1) to yield methyl trans-4-(dibenzylamino)cyclohexanecarboxylate as white needles (0.33 g).

Step B methyl trans-4-(dibenzylamino)cyclohexanecarboxylate (0.22 g) was dissolved in anhydrous THF (2.2 ml) and cooled to 0° C. Lithium aluminum hydride (0.125 g) was added portionwise over ca. 15 minutes. When foaming ceased batch temperature was slowly increased and reaction accelerated (exothermic). After 30 minutes sampled for TLC (DCM) and no starting material was detected. Reaction mixture was quenched with water and 10% NaOH. Phases were separated. Aqueous was extracted with methyl r-butyl ether. The combined organic phases were washed with brine, dried over anhydrous sodium sulfate and concentrated in vacuo to yield [trans-4-(dibenzylamino)cyclohexyl]methanol as a colorless oil solidifying upon standing (0.20 g). The crude product obtained was used without further purification.

Step C

[trans-4-(dibenzylamino)cyclohexyl]methanol (7.74 g) and triphenylphosphine (9.84 g) were dissolved in anhydrous THF (60 ml). Tetrabromomethane (12.44 g) was dissolved in THF (17.5 ml) and added dropwise to the reaction mixture. The flask was cooled with water (~10° C.) due to exothermicity. Precipitate appeared. After 1 hour sampled for TLC (DCM 100%) that revealed completed reaction. The solvent was evaporated and the residue purified by chromatography on silica gel (DCM 100%). Fractions containing product were combined and evaporated. Solid residue was taken with hexane (30 ml) and cooled to 2 to 4° C. The precipitate was filtered off, rinsed with cold hexane and dried under vacuum to yield N,N-dibenzyl-trans-4-(bromomethyl)cyclohexanamine as a white solid (9.2 g).

Step D

N,N-dibenzyl-trans-4-(bromomethyl)cyclohexanamine (5.0 g) was suspended in isopropyl alcohol (10 ml). $Na_2SO_3$ (2.2 g) and KI (cat) were dissolved in water (20 ml) and added to the suspension of N,N-dibenzyl-4-(bromomethyl)cyclohexanamine in a pressure reactor. It was sealed and heated to 130° C. with good agitation. Reaction progress was controlled by TLC (DCM 100%). When reaction was found to be completed, solvents were evaporated and dried by azeotropic distillation with toluene to yield [trans-4-(dibenzylamino)cyclohexyl] methanesulfonic acid. The crude product obtained was used without further purification.

Step E

Crude [trans-4-(dibenzylamino)cyclohexyl]methanesulfonic acid (4.5 g) was suspended in chloroform (75 ml) and cooled in an ice bath. Thionyl chloride (19.4 ml) was added dropwise. Reaction mixture was agitated for 20 minutes at RT then heated to 65° C. and agitated at 65° C. overnight. Solvent and excess of thionyl chloride were evaporated to afford [trans-4-(dibenzylamino)cyclohexyl]methanesulfonyl chloride. The crude product obtained was used without further purification.

Step F

Crude [trans-4-(dibenzylamino)cyclohexyl]methanesulfonyl chloride (~11.5 mmol) was suspended in anhydrous THF (45 ml) and cooled to 0° C. Triethylamine (2.4 ml) was added followed by methylamine (2M in THF, 11.5 ml). Reaction mixture was agitated at 0° C. for 1 hour, warmed to RT and held for 1 hour at RT. The solvent was evaporated and the residue was taken with EtOAc (100 ml) and washed with NaHCO₃ (sat.). Aqueous phase was backwashed with EtOAc (50 ml). The combined organic phases were washed with water and brine (50 ml each), dried over magnesium sulfate and concentrated in vacuo. The crude material was purified by chromatography on silica gel (DCM/MeOH 8:1). Fractions containing product were combined, concentrated in vacuo and triturated with DCM/hexane (1:1). Precipitate was filtered out, washed with cold DCM/hexane (1:1) and dried under vacuum to yield 1-[trans-4-(dibenzylamino)cyclohexyl]-N-methyl-methanesulfonamide as a white solid (1.67 g).

Step G

1-[trans-4-(dibenzylamino)cyclohexyl]-N-methyl-methanesulfonamide (1.6 g) was dissolved (partially) m MeOH (16 ml). Ammonium formate (1.04 g) and wet 10% Pd/C (0.3 g) were added. Reaction mixture was heated to reflux with good agitation. Very stow conversion was encountered (TLC-DCM/MeOH 8:1). Solvent was topped up with THF (10 ml). Another portion of ammonium formate (1.04 g) was added followed by 10% Pd(OH)₂/C (0.3 g). Reaction mixture was resampled for TLC (DCM/McOH 8:1) after 1 hour—full conversion was noted. The palladium catalyst was filtered out through a plug of Celite. The filter cake was washed with MeOH (2×20 ml). Filtrates were combined and evaporated. Solid residue was taken with methanol and evaporated (to remove remaining aromatic volatiles and ammonium formate). This step was repeated twice to give 1-(trans-4-aminocyclohexyl)-N-methyl-methanesulfonamide as an off-white solid (0.85 g).

Step H

To a suspension of 4-Chloro-7-azaindole (1.37 g), triethylamine (1.9 ml) and DMAP (0.11 g) in DCM (70 ml) wax added at RT benzenesulfonyl chloride (1.3 ml). The reaction mixture was stirred at RT overnight. The reaction mixture was diluted with DCM and was quenched with an aqueous solution of HCl (1M, 70 ml). The organic phase was separated and extracted with a saturated solution of NaHCO₃ (70 ml), with water and with a saturated aqueous solution of NaCl, dried over Na₂SO₄ and concentrated in vacuo to yield 1-(benzenesulfonyl)-4-chloro-pyrrolo[2,3-b]pyridine as a brown solid (2.65 g). The crude product obtained was used without further purification.

Step I

Tetrabutylammonium nitrate (381 mg) dissolved in DCM (5 ml) was added dropwise to a solution of 1-(benzenesulfonyl)-4-chloro-pyrrolo[2,3-b]pyridine (292 mg) in DCM (5 ml) under nitrogen at −10° C. Trifluoroacetic anhydride (180 μl) was added dropwise, stirred for 30 minutes at the same temperature and then for 4 hours at RT. Additional tetrabutylammonium nitrate (80 mg) and trifluoroacetic anhydride (40 μl) were added and the reaction mixture was stirred at room temperature overnight. Additional tetrabutylammonium nitrate (380 mg) and trifluoroacetic anhydride (180 μl) were added and the reaction mixture was stirred at room temperature for 3 hours. After diluting with DCM, the reaction mixture was quenched with water. The organic phase was separated and extracted 3 times with water and once with a saturated aqueous solution of NaCl, dried over Na₂SO₄ and concentrated in vacuo. Ille crude product was purified by chromatography on silica gel (EtOAc/heptane 1:5) to yield 1-(benzenesulfonyl)-4-chloro-5-nitro-pyrrolo[2,3-b]pyridine as a beige solid (111 mg).

Step J 1-(benzenesulfonyl)-4-chloro-5-nitro-pyrrolo[2,3-b]pyridine (337 mg), 1-(trans-4-aminocyclohexyl)-7V-methyl-methanesulfonamide (example 1, step G, 206 mg) and potassium carbonate (304 mg) were suspended in dioxan/water 9:1 (10 ml). The resulting suspension was heated to 120° C. in a microwave oven. After 2 hours, the reaction mixture was sampled for HPLC/MS—no starting material visible; product was formed. The reaction mixture was concentrated in vacuo. THF (15 ml), EtOAc (45 ml) and water (30 ml) were added to the residue. The reaction mixture was stirred at RT for 30 minutes. The aqueous phase was separated and extracted twice with a mixture of THF/EtOAc 1:3. The combined organic phases were extracted with a saturated aqueous solution of NaCl, dried over Na₂SO₄ and concentrated in vacuo. The crude product was purified by chromatography on silica gel (EtOAc/heptane 1:1 to EtOAc 100%) to yield 1-[trans-4 [[1-(benzenesulfonyl)-5-nitro-1H-pyrrolo[2,3-b]pyridin-4-yl]amino]cyclohexyl]-N-methyl-methanesulfonamide as a yellow foam (276 mg).

Step K

1-[trans-4-[[1-(benzenesulfonyl)-5-nitro-1H-pyrrolo[2,3-b]pyridin-4-yl]amino]cyclohexyl]-N-methyl-methanesulfonamide (254 mg) was dissolved in THF (20 ml). This solution was hydrogenated for 6 hours over a Raney-Nickel catalyst using the H-Cube® flow reactor (Full H₂-Mode, temperature=RT, flow rate=1 ml/min). The THF was removed under vacuum. The residue was dissolved in EtOAc, dried over magnesium sulfate and concentrated in vacuo to yield 1-[trans-4-[[5-amino-1-(benzenesulfonyl)-1H-pyrrolo[2,3-b]pyridin-4-yl]amino]cyclohexyl]-W- methyl-methanesulfonamide as a yellow resin (222 mg). The crude product obtained was used without further purification.

Step L

A mixture of 1-[trans-4-[[5-amino-1-(benzenesulfonyl)-1H-pyrrolo[2,3-b]pyridin-4-yl]amino]cyclohexyl]-N-methyl-methanesulfonamide (95 mg), triethyl orthoformate (80 µl) and p-toluenesulfonic acid monohydrate (4 mg) in toluene (6 ml) was refluxed overnight.
After diluting with EtOAc, the reaction mixture was quenched with a saturated aqueous solution of NaHCO$_3$. The organic phase was separated and was extracted once again with with a saturated aqueous solution of NaHCO$_3$ and with a saturated aqueous solution of NaCl, dried over MgSO$_4$ and concentrated in vacuo. The crude product was purified on a semi-preparative HPLC to yield 1-[trans-4-(6-(phenylsulfonyl)-imidazo[4,5-d]pyrrolo[2,3-b]pyridin-1(6H)-yl)cyclohexyl]-N-methylmethanesulfonamide as a colorless resin (50 mg).

Step M

A mixture of 1-[trans-4-(6-(phenylsulfonyl)-imidazo[4,5-d]pyrrolo[2,3-b]pyridin-1(6H)-yl)cyclohexyl]-N-methyl-methanesulfonamide (68 mg) and lithium hydroxide (14 mg) in isopropanol/water 1:1 (1 ml) was stirred at 40° C. overnight. After 20 hours, the reaction mixture was heated to 50° C. and stirred at 50° C. for one day.
Additional lithium hydroxide (14 mg) was added. The reaction mixture was heated to 60° C. and stirred at 60° C. for one day. An aqueous solution of HCl 37% (120 µl) was added until pH=5 was reached and then a saturated aqueous solution of NaHCO$_3$ (100 µl) was added until pH=8 was reached. Isopropanol was evaporated. EtOAc/THF (2-3 ml) was added to the residue and the resulting suspension was stirred at room temperature. An aqueous solution of potassium carbonate (2 M, 2-3 ml) was added until pH=12 was reached. The suspension was further stirred at room temperature and the precipitate was filtered off rinsed with water and dried under vacuum to yield 1-[trans-4-(imidazo[4,5-d]pyrrolo[2,3-b]pyridin-1(6H)-yl)cyclohexyl]-N-methylmethanesulfonamide (13 mg, compound 22 in Table 1). MS (HPLC/MS): 348 (MH$^+$). Retention time: 1.70 min.

EXAMPLE 2

This example illustrates the preparation of N-methyl-1-[trans-4-[(5-nitro-1H-pyrrolo[2,3-b]pyridin-4-yl)oxy]cyclohexyl]methanesulfonamide (Compound 25 in Table 1)

Step A

Ethyl trans-4-hydroxycyclohexanecarboxylate (10 g), diisopropylamine (21 ml), benzyl bromide (10 ml) and sodium iodide (0.9 g) were mixed together and heated in a sealed tube at 120° C. overnight. After diluting with EtOAc, the reaction mixture was quenched with water. The aqueous phase was separated and extracted twice with EtOAc. The combined organic phases were dried over anhydrous MgSO$_4$ and concentrated in vacuo. The crude product was purified by chromatography on silica gel (hexane/EtOAc 9:1) to yield ethyl trans-4-(benzyloxy)cyclohexanecarboxylate as a yellow oil (16.0 g).

Step B

Ethyl trans-4-(benzyloxy)cyclohexanecarboxylate (16.0 g) was suspended in dry THF while cooling in an ice bath. Lithium aluminum hydride (5.2 g) was added portionwise. After addition reaction mixture was heated at 60° C. for 4 hours. After that time the reaction mixture was cooled to 0° C. and EtOAc (30 ml) followed by water (30 ml) were added. The resulting inorganic salts were filtered off through a pad of Celite. Phases were separated. Aqueous was extracted with EtOAc. The combined organic phases were dried over anhydrous MgSO$_4$ and concentrated in vacuo to yield (trans-4-benzyloxycyclohexyl)methanol as a light yellow solid (14.2 g). The crude product obtained was used without further purification.

Step C (trans-4-benzyloxycyclohexyl)methanol (14.2 g) was suspended in dry THF while cooling in an ice bath. Triphenylphosphine (22.32 g) was added. The resulting solution was stirred at 0° C. for 10 minutes, then tetrabromomethane (28.22 g) was added portionwise and the slurry was allowed to reach room temperature. After 24 hours of stirring the white precipitate was filtered and washed with THF followed by EtOAc. The filtrate was evaporated under reduced pressure and purified by column chromatography on silica gel (hexane/EtOAc 9:1) to yield benzyl trans-4-(bromomethyl)cyclohexyl ether as a yellow solid (17.0 g).

Step D benzyl trans-4-(bromomethyl)cyclohexyl ether (8.0 g) was dissolved in isopropanol (100 ml) and sodium sulphite (7.12 g) in water (100 ml) was added. The reaction mixture was then stirred vigorously while heated at 100° C. overnight. After cooling to room temperature, the reaction mixture was concentrated to give a white solid. Methanol was added and the mixture was stirred at RT for 3 hours, then the precipitate was filtered off, rinsed with methanol, the filtrate was evaporated to yield (trans-4-benzyloxycyclohexyl)methanesulfonic acid as a white solid (9.5 g).

Step E (trans-4-benzyloxycyclohexyl)methanesulfonic acid (1.0 g) was suspended in a freshly distilled chloroform (50 ml) while cooling m an ice bath. Dry DMF (3-5 drops) was added. The resulting solution was stirred at 0° C. for 10 minutes, then thionyl chloride (0.52 ml) was added drop wise. The mixture was stirred at this temperature for 15 minutes, 30 minutes at room temperature and overnight at 45° C. After cooling down, the solvent was evaporated; dry DCM was added and evaporated to remove the residual thionyl chloride. This procedure was repeated twice to yield (trans-4-benzyloxycyclohexyl)methanesulfonyl chloride as a yellow oil (1.0 g).

Step F (trans-4-benzyloxycyclohexyl)methanesulfonyl chloride (1.0 g) was suspended m dry DCM (50 ml) while cooling in an ice bath, methylamine (2M in THF, 5.0 ml) was added drop wise. Subsequently, the reaction mixture was allowed to reach room temperature and stirred at this temperature overnight. After that time, the solvent was evaporated and purified by column chromatography on silica gel (hexane/EtOAc 9:1) to yield 1-(trans-4-benzyloxycyclohexyl)-N-methyl-methanesulfonamide as a light yellow solid (0.56 g).

Step G 1-(trans-4-benzyloxycyclohexyl)-N-methyl-methanesulfonamide (3.7 g) was suspended in methanol, Pd(OH)$_2$ (1.75 g) was added. Subsequently, the reaction was continued in a Parr apparatus for 12 hours. Then, the catalyst was filtered off through a pad of Celite. Filtrate was evaporated, washed with Et$_2$O and dried under vacuum to yield 1-(trans-4-hydroxycyclohexyl)-N-methyl-methanesulfonamide as a white solid (2.44 g).

Step H

Sodium hydride (60% in mineral oil, 0.09 g) was added under nitrogen to a solution of 1-(trans-4-hydroxycyclohexyl)-N-methyl-methanesulfonamide (0.40 g) in DMF (19 ml). After 30 minutes at room temperature, 2-(trimethylsilyl) ethoxymethyl chloride was added over 15 minutes to the reaction mixture. After 18 hours at room temperature, the reaction mixture was diluted with EtOAc and quenched with an aqueous solution of sodium phosphate (1 M). The aqueous phase was separated and extracted twice with EtOAc. The combined organic phases were washed with water and twice with brine, dried over anhydrous magnesium sulfate and concentrated in vacuo to yield 1-(trans-4-hydroxycyclohexyl)-N-methyl-N-(2-trimethylsilylethoxymethyl)methanesulfonamide as a yellow oil (0.66 g). The crude product obtained was used without further purification.

Step I

Sodium hydride (60% in mineral oil, 0.07 g) was added under nitrogen to a solution of 1-(trans-hydroxycyclohexyl)-N-methyl-N-(2-trimethylsilylethoxymethyl)methanesulfonamide (0.49 g) in DMF (10 ml). After 30 minutes at room temperature, 1-(benzenesulfonyl)-4-chloro-5-nitro-pyrrolo[2,3-b]pyridine (example 1, step I, 0.49 g) in DMF (5 ml) was added over 15 minutes to the reaction mixture. After three days at room temperature, EtOAc was added mid the reaction mixture was poured onto water. The aqueous phase was separated and extracted with EtOAc. The combined organic phases were washed twice with water, twice with an aqueous sodium hydroxide solution (2 N) and twice with brine, dried over anhydrous magnesium sulfate and concentrated in vacuo. The crude product was purified on a semi-preparative HPLC to yield N-methyl-1-[trans-4-[(5-nitro-1H-pyrrolo[2,3-b]pyridin-4-yl)oxy]cyclohexyl]-N-(2-trimethylsilylethoxymethyl)methanesulfonamide as a yellow solid (0.12 g).

Step J

A solution of N-methyl-1-[trans-4-[(5-nitro-1H-pyrrolo[2,3-b]pyridin-4-yl)oxy]cyclohexyl]-N-(2-trimethylsilylethoxymethyl)methanesulfonamide (120 mg) in AcOH (10 ml) and water (5 ml) was stirred at 70° C. for 1 hour under nitrogen. The reaction mixture was cooled to room temperature and poured onto water. An aqueous solution of NaOH (4N) was added until pH=7-8 was reached. The aqueous phase was extracted twice with EtOAc. The Combined organic phases were washed with water, twice with an aqueous sodium hydroxide solution (2 N) and with brine, dried over anhydrous magnesium sulfate and concentrated in vacuo. The residue was recrystallized from DCM/EtOAc (9:1) to yield N-methyl-1-[trans-4-[(5-nitro-1H-pyrrolo[2,3-b]pyridin-4-yl)oxy]cyclohexyl]methanesulfonamide (50 mg, compound 25 in Table 1). MS (HPLC/MS): 369 (MH$^+$). Retention time: 1.12 min.

EXAMPLE 3

This example illustrates the preparation of 1-[trans-4-[(5-cyano-1H-pyrrolo[2,3-b]pyridin-4-yl)-methyl-amino]cyclohexyl]-N-methyl-methanesulfonamide (Compound 26 in Table 1).

Step A

Sodium bis(2-methoxyethoxy)aluminum hydride solution (Red-Al®, 65% in toluene, 183 ml) is added over 60 minutes to a solution of trans-4-(tert-butoxycarbonylamino)cyclohexanecarboxylic acid (24.3 g) in toluene (250 ml) at 0° C. The reaction mixture was then heated to 130° C. and stirred at this temperature for 1 hour. After cooling to 0° C., a saturated aqueous solution of sodium sulfate (195 ml) was added drop wise. The reaction mixture was then filtered off through a Hyflo fitter. The fitter cake was rinsed with DCM (150 ml) and water (24 ml). The aqueous phase was separated and extracted twice with DCM (2×150 ml). The combined organic phases were dried over anhydrous magnesium sulfate and concentrated in vacuo to yield [trans-4-(methylamino)cyclohexyl]methanol as white crystals (12.5 g). The crude product obtained was used without further purification.

Step B

Benzoyl chloride (8.8 ml) was added dropwise to an emulsion of sodium hydrogencarbonate (12.6 g) in water (50 ml) and [trans-4-(methylamino)cyclohexyl]methanol (10.9 g) in DCM (50 ml) at 0° C. Subsequently, the reaction mixture was allowed to reach room temperature and stirred at this temperature for 3 hours. The reaction mixture was diluted with water (150 ml) and with DCM (200 ml). The organic phase was separated, dried over anhydrous magnesium sulfide and concentrated in vacuo to yield N-[trans-4-(hydroxymethyl)cyclohexyl]-N-methylbenzamide as beige crystals (17.2 g). The crude product obtained was used without further purification.

Step C

Triethylamine (11 ml), DMAP (0.43 g) and p-toluenesulfonyl chloride (13.2 g) were added to a solution of N-[trans-4-(hydroxymethyl)cyclohexyl]-N-methylbenzamide (17.0 g) in DCM (250 ml). After 3 hours at room temperature, the reaction mixture was quenched with water (150 ml). The organic phase was separated, dried over anhydrous magnesium sulfate and concentrated in vacuo. The crude product was purified by chromatography on silica gel (EtOAc/heptane 1:1) to yield [trans-4-[benzoyl(methyl)amino]cyclohexyl]methyl 4-methylbenzenesulfonate as white crystals (19.5 g).

Step D

Potassium thioacetate (6.3 g) was added to a suspension of [trans-4-[benzoyl(methyl)amino]cyclohexyl]methyl 4-methylbenzenesulfonate (19.5 g) in DMSO (66 ml) at RT. The reaction mixture was heated to 55° C. and stirred at 55° C. for 3 hours. After cooling down at room temperature, the reaction mixture was diluted with EtOAc (200 ml) and quenched with an aqueous solution of NaHCO$_3$ (0.1 M, 300 ml). The aqueous phase was separated and extracted twice with EtOAc (2×200 ml). The combined organic phases were washed with water and brine, dried over anhydrous magnesium sulfate and concentrated in vacuo. The residue (17 g, light yellow crystals) was dissolved in formic acid (73 ml) and the reaction mixture was heated to 25-35° C. A hydrogen peroxide solution (30% in water, 25 ml) was added over 60 minutes at this temperature. Subsequently, the reaction mixture was cooled down at room temperature and stirred at RT for 15 minutes. After cooling down at 0° C., the reaction mixture was quenched with an aqueous solution of sodium metabisulfite (33%, 27 ml). An aqueous solution of NaOH (33%, 121 ml) was then added at 0° C. until pH=5 was reached and the reaction mixture was stirred at RT overnight. The reaction mixture was concentrated in vacuo. The residue obtained was taken up in water (160 ml) and 2-propanol (40 ml) and stirred at 45° C. Subsequently, 2-propanol was evaporated and an aqueous solution of HCl (2 M, 10 ml) was added. The suspension was stirred at 0° C. and filtered off. The precipitate was dried under vacuum over Sicapent® to yield [trans-4-[benzoyl(methyl)amino] cyclohexyl]methanesulfonic acid as a white solid (31.0 g) used in the next step without further purification.

Step E

[trans-4-[benzoyl(methyl)amino]cyclohexyl]methanesulfonic acid (10.1 g) was suspended in DCM (40 ml) with addition of a few drops of DMF. The reaction mixture was cooled down at 0° C. and thionyl chloride (4.7 ml) was added drop wise over 10 minutes. The reaction mixture was then refluxed for 6 hours. After cooling down at 0° C., additional thionyl chloride (4.7 ml) was added drop wise over 10 minutes. The reaction mixture was then refluxed overnight. After that time, the mixture was cooled to room temperature and concentrated nearly to dryness in vacuo. Dry toluene was added to the residue and removed under reduced pressure to ensure the removal of any unreacted thionyl chloride. The residue was taken up in THF (40 ml) and methylamine was added (2 M in THF, 47 ml). The reaction mixture was stirred at RT overnight. The resulting suspension was filtered and rinsed with THF. The filtrate was evaporated to afford a light brown resin (2.6 g). The precipitate was suspended in DCM (20 ml) with addition of a few drops of DMF. Thionyl chloride (2.4 ml) was added dropwise over 10 minutes. The reaction mixture was then refluxed overnight. After 16 hours under reflux, additional thionyl chloride (2.4 ml) was added dropwise over 10 minutes. The reaction mixture was then refluxed overnight. After that time, the mixture was cooled to room temperature and concentrated nearly to dryness in vacuo. Dry toluene was added to the residue and removed under reduced pressure to ensure the removal of any unreacted thionyl chloride. The residue was taken up in THF (20 ml) and methylamine was added (2 M in THF, 24 ml). The reaction mixture was stirred at RT for 4 hours, then was filtered and rinsed with THF. The filtrate was evaporated to afford a light brown resin (2.0 g). The combined light brown resins (4.6 g) were purified by chromatography on silica gel (McOH/DCM 1:49 to 1:19) to yield N-methyl-N-[trans-4-(methylsulfamoylmethyl)cyclohexyl]benzamide as beige crystals (2.18 g).

Step F

N-methyl-N-[trans-4-(methylsulfamoylmethyl)cyclohexyl]benzamide (875 mg) was taken up in an aqueous solution of HCl (6 M, 10 ml) and the reaction mixture was refluxed for two days. After cooling down at room temperature, the resulting suspension was filtered. The filtrate was concentrated in vacuo to yield N-methyl-1-[trans-4-(methylamino)cyclohexyl]methanesulfonamide hydrochloride as beige crystals (710 mg). The crude product obtained was used without further purification.

Step G

N-methyl-1-[trans-4-(methylamino)cyclohexyl]methanesulfonamide hydrochloride (129 mg), 4-Chloro-1H-pyrrolo [2,3-b]pyridine-carbonitrile (89 mg) and potassium carbonate (225 mg) were suspended in water/dioxane 1:9 (4.5 ml). The resulting suspension was heated to 160° C. in a microwave oven for 8 hours. The reaction mixture was concentrated in vacuo. The residue was taken up in THF (10 ml) and a mixture of water/aqueous saturated solution of NaCl 1:1 (20 ml) was added. The mixture was stirred at RT. The aqueous phase was separated and extracted twice with THF (2×10 ml). The combined organic phases were washed with brine, dried over anhydrous magnesium sulfate and concentrated in vacuo. The residue was suspended in acetonitrile, stirred at RT, filtered and rinsed with acetonitrile. The filtrate was concentrated in vacuo and was purified on a semi-preparative HPLC to yield 1-[trans-4-[(5-cyano-1H-pyrrolo [2,3-b]pyridin-4-yl)-methyl-amino]cyclohexyl]-N-methyl-methanesulfonamide (22 mg, compound 26 in Table 1). MS (HPLC/MS): 362 (MH$^+$). Retention time: 2.19 min.

EXAMPLE 4

This example illustrates the preparation of N-methyl-1-[trans-4-[methyl(9H-purin-6-yl)amino]cyclohexyl]methanesulfonamide (Compound 2 in Table 1).

Step A

N-methyl-1-[trans-4-(methylamino)cyclohexyl]methanesulfonamide hydrochloride (example 3, step F, 140 mg), 6-chloropurine (59 mg) and triethylamine (0.26 ml) were dissolved in n-butanol (4 ml). The reaction mixture was heated to 140° C., stirred at 140° C. overnight and heated to 150° C. in a microwave oven for 1 hour. The reaction mixture was concentrated in vacuo. The residue was taken up in THF (3 ml) and a mixture of water/aqueous saturated solution of NaCl 1:1 (4 ml) was added. The mixture was stirred at RT. The aqueous phase was separated and extracted twice with THF (2×3 ml). The combined organic phases were washed with brine, dried over anhydrous magnesium sulfate and concentrated in vacuo. The residue was purified first by chromatography on Isolute® NH$_2$ (DCM 100%, McOH/DCM 1:49 to 1:19), then on a semi-preparative HPLC and finally by chromatography on Isolute® NH$_2$ (MeOH/DCM 1:24) to yield N-methyl-1-[trans-4-[methyl (9H-purin-6-yl)amino]cyclohexyl]methanesulfonamide (22 mg, compound 2 in Table 1). MS (HPLC/MS): 339 (MH$^+$). Retention time: 1.87 min.

EXAMPLE 5

This example illustrates the preparation of 1-[4-[(2-amino-5-methyl-pyrimidin-4-yl)-methyl-amino]cyclohexyl]-N-methyl-methanesulfonamide (Compound 29 in Table 1).

Step A

N-methyl-1-[trans-4-(methylamino)cyclohexyl]methanesulfonamide hydrochloride (example 3, step F, 129 mg), 4-chloro-5-methyl-pyrimidin-2-amine (72 mg), $Cs_2CO_3$ (390 mg), $Pd(OAc)_2$ (11 mg) and RuPhos (47 mg) were dissolved in tert-butanol (1 ml) in a schlenk tube. The reaction mixture was heated to 85° C., stirred at 85° C. overnight. The reaction mixture was taken up in THF (10 ml) and filtered over celite. The filtrate was concentrated in vacuo. The residue was purified on a semi-preparative HPLC to yield 1-[4-[(2-amino-5-methyl-pyrimidin-4-yl)-methyl-amino]cyclohexyl]-N-methyl-methanesulfonamide (Compound 29 in Table 1). MS (HPLC/MS): 328 ($MH^+$). Retention time: 1.82 min.

EXAMPLE 6

This example illustrates the preparation of 1-[trans-4-((2-methoxymethyl)imidazo[4,5-d]pyrrolo[2,3-b]pyridin-1(6H)-yl)cyclohexyl]-N-methylmethanesulfonamide (Compound 35 in Table 1).

Step A

A mixture of 1-[trans-4-[[5-amino-1-(benzenesulfonyl)-1H-pyrrolo[2,3-b]pyridin-4-yl]amino]cyclohexyl]-N-methyl-methanesulfonamide (Example 1, step K) (212 mg), methoxyacetyl chloride (40 µl) and triethylamine (70 µl) in methylenchloride (5 ml) was stirred an hour at room temperature. The reaction mixture is concentrated in vacuo. The crude is taken up in acetic acid (2 mL) and heated at 100° C. for 3 h in a microwave. After diluting with EtOAc, the reaction mixture was quenched with a saturated aqueous solution of $NaHCO_3$. The organic phase was separated and was extracted once again with with a saturated aqueous solution of $NaHCO_3$ and with a saturated aqueous solution of NaCl, dried over $MgSO_4$ and concentrated in vacuo. The crude product was purified on a semi-preparative HPLC to yield 1-[trans-4-<(2-methoxymethyl)-6-(phenylsulfonyl)-imidazo[4,5-d]pyrrolo[2,3-b]pyridin-1(6H)-yl Cyclohexyl]-N-methylmethanesulfonamide as a colorless resin.

Step B

1-[trans-4-((2-methoxymethyl)-6-(phenylsulfonyl)-imidazo[4,5-d]pyrrolo[2,3-b]pyridin-1(6H)-yl)cyclohexyl]-N-methylmethanesulfonamide is deprotected using a similar procedure as described in Example 1, step 1, to yield 1-[trans-4-((2-methoxymethyl)imidazo[4,5-d]pyrrolo[2,3-b]pyridin-1(6H)-yl)cyclohexyl]-N-methylmethanesulfonamide (26 mg, compound 35 in Table 1). MS (HPLC/MS): 392 ($MH^+$). Retention time: 1.89 min.

Analysis of the purified samples is m each case done using a Waters Autopurification (HPLC/MS) system with a reversed phase column (Daisogel SP-120-ODS-AP 5 µm, 150×3 mm) from Bischoff, Leonberg, Germany. The samples are characterized by m/z and retention time. The above-given retention times relate in each case to the use of a solvent system comprising two different solvents, solvent A: $H_2O$+0.01% HCOOH, and solvent B: $CH_3CN$+0.01% HCOOH). Said two solvents A and B are employed at a flow rate of 2.00 ml/min with a time-dependent gradient as given in the Table:

Method A: column Daisogel SP-120-ODS-AP 5 µm, 150×3 mm) from Bischoff, Leonberg, Germany, flow rate of 2.00 mL/min with a time-dependent gradient as given in Table 1:

TABLE 1

| Time [min] | A [%] | B [%] |
| --- | --- | --- |
| 0.5 | 90 | 10 |
| 1.0 | 74 | 26 |
| 1.5 | 60 | 40 |
| 2.0 | 47 | 53 |
| 2.5 | 36 | 64 |
| 3.0 | 26 | 74 |
| 3.5 | 19 | 81 |
| 4.0 | 13 | 87 |
| 4.25 | 10 | 90 |
| 4.5 | 8 | 92 |
| 4.75 | 7 | 93 |
| 5.0 | 6 | 94 |
| 5.5 | 5 | 95 |
| 6.5 | 5 | 95 |

Method B: column Waters XTerra MS C18 5 µm, 50×4.6 mm (Waters), flow rate of 3.00 mL/min with a time-dependent gradient as given in Table 2

TABLE 2

| Time [min] | A [%] | B [%] |
| --- | --- | --- |
| 0 | 90 | 10 |
| 0.5 | 90 | 10 |
| 2.5 | 5 | 95 |
| 2.8 | 5 | 95 |
| 2.9 | 90 | 10 |
| 3.0 | 90 | 10 |

The substances named in the following Table 3 are prepared analogously to the above-described methods. The following physical data are obtained according to the above-described HPLC/MS characterization process.

TABLE 3

| Ex. No. | Compound of formula | m/z: [M + $H^+$] | $R_t$ [min] (Method) | Physical state |
| --- | --- | --- | --- | --- |
| 1 | 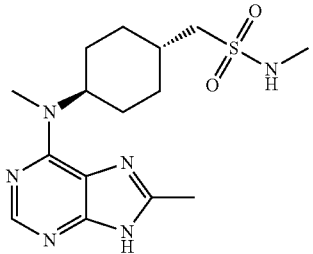 | 353 | 1.72 (A) | solid |

TABLE 3-continued

| Ex. No. | Compound of formula | m/z: [M + H⁺] | R$_t$ [min] (Method) | Physical state |
|---|---|---|---|---|
| 2 | | 339 | 1.87 (A) | solid |
| 3 | | 339 | 1.80 (A) | solid |
| 4 | | 415 | 3.80 (A) | solid |
| 5 | | 429 | 3.50 (A) | solid |
| 6 | | 325 | 1.38 (B) | solid |

TABLE 3-continued

| Ex. No. | Compound of formula | m/z: [M + H⁺] | R$_t$ [min] (Method) | Physical state |
|---|---|---|---|---|
| 7 | | 392 | 1.80 (A) | resin |
| 8 | | 341 | 2.08 (A) | solid |
| 9 | | 355 | 2.08 (A) | solid |
| 10 | | 348 | 2.26 (A) | resin |
| 11 | | 300 | 1.71 (A) | solid |
| 12 | | 314 | 1.83 (A) | solid |

TABLE 3-continued

| Ex. No. | Compound of formula | m/z: [M + H+] | R$_t$ [min] (Method) | Physical state |
|---|---|---|---|---|
| 13 | | 378 | 1.84 (A) | solid |
| 14 | | 365 | 2.53 (A) | solid |
| 15 | | 324 | 1.95 (A) | solid |
| 16 | | 314 | 1.89 (A) | resin |
| 17 | | 379 | 2.67 (A) | solid |
| 18 | | 382 | 2.38 (A) | solid |

TABLE 3-continued

| Ex. No. | Compound of formula | m/z: [M + H⁺] | R$_t$ [min] (Method) | Physical state |
|---|---|---|---|---|
| 19 | | 342 | 1.33 (B) | solid |
| 20 | | 366 | 1.37 (B) | oil |
| 21 | | 390 | 2.26 (A) | oil |
| 22 | | 348 | 1.70 (A) | solid |
| 23 | | 376 | 2.28 (A) | solid |
| 24 | | 362 | 2.72 (A) | solid |

TABLE 3-continued

| Ex. No. | Compound of formula | m/z: [M + H+] | R_t [min] (Method) | Physical state |
|---|---|---|---|---|
| 25 | | 369 | 1.12 (B) | solid |
| 26 | | 362 | 2.19 (A) | solid |
| 27 | | 348 | 2.75 (A) | solid |
| 28 | | 328 | 1.95 (A) | foam |
| 29 | | 328 | 1.82 (A) | foam |
| 30 | | 368 | 2.50 (A) | solid |

TABLE 3-continued

| Ex. No. | Compound of formula | m/z: [M + H+] | R_t [min] (Method) | Physical state |
|---|---|---|---|---|
| 31 | 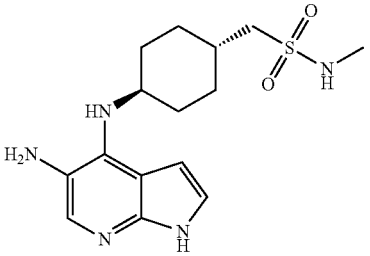 [SMILES: CNS(=O)(=O)C[C@H]1CC[C@H](Nc2c(N)cnc3[nH]ccc23)CC1] | 338 | 0.29 (B) | foam |
| 32 | 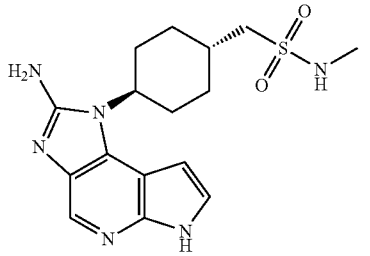 [SMILES: CNS(=O)(=O)C[C@H]1CC[C@H](n2c(N)nc3cnc4[nH]ccc4c32)CC1] | 363 | 1.67 (A) | solid |
| 33 | 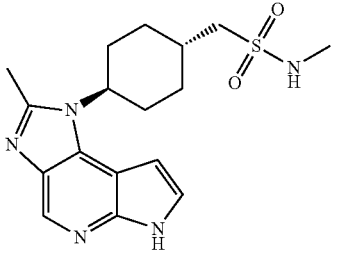 | 362 | 1.71 (A) | solid |
| 34 | 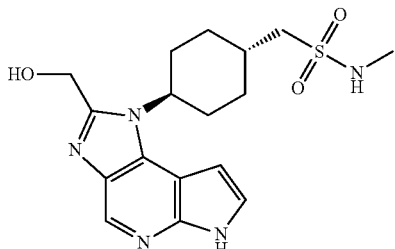 | 378 | 1.63 (A) | solid |
| 35 | 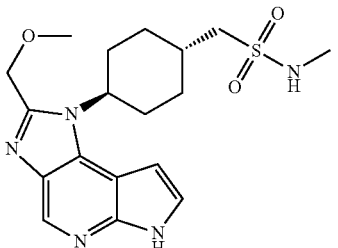 | 392 | 1.89 (A) | foam |

Measurement of the Effect on the JAK Enzyme

All four kinases of the JAK/TYK-kinase family were used as purified recombinant GST-fusion proteins, containing the active kinase domains. GST-JAK1(866-1154), GST-JAK3 (811-1124), and GST-TYK2(888-1187) were expressed and purified by affinity chromatography at the EPK biology unit.

The kinase assays were based on the Caliper mobility shift assay using the LabChip 3000 systems. This technology is similar to capillary electrophoresis and uses charge driven separation of substrate and product in a microfluidic chip.

All kinase reactions were performed in 384 well microtiter plates in a total reaction volume of 18 µl. The assay plates were prepared with 0.1 µl per well of test compound in the appropriate test concentration, as described under the section "preparation of compound dilutions". The reactions were started by combining 9 µl of substrate mix (consisting of peptide and ATP) with 9 µl of kinase dilution. The reactions were incubated for 60 minutes at 30° C. and stopped by adding 70 µl of stop buffer (100 mM Hepes, 5% DMSO, 0.1% Coating reagent, 10 mM EDTA, 0.015% Brij 35).

Fluorescently labeled synthetic peptides were used as substrates in all reactions. A peptide derived from the sequence of IRS-1 (IRS-1 peptide, FITC-Ahx-KKSRGDYMTMQIG-NH2) was used for JAK1 and TYK2 and a peptide named JAK3tide (FITC-GGEEEEYFELVK-KKK-NH2) for JAK3. Specific assay conditions are described in Table 4:

TABLE 4

Assay conditions of individual kinase assays

| Kinase | JAK1 | JAK3 | TYK2 |
|---|---|---|---|
| Buffer | 50 mM Hepes pH 7.5, 0.02% Tween 20, 1 mM DTT, 0.02% BSA, 12 mM MgCl2 | 50 mM Hepes pH 7.5, 0.02% Tween 20, 1 mM DTT, 0.02% BSA, 1.5 mM MgCl2 | 50 mM Hepes pH 7.5, 0.02% Tween 20, 1 mM DTT, 0.02% BSA, 9 mM MgCl2 |
| DMSO | 0.6% | 0.6% | 0.6% |
| Kinase conc. | 50 nM | 6 nM | 40 nM |
| Substrate peptide conc. | 5 µM | 2 µM | 5 µM |
| ATP conc. | 40 µM | 80 or 18 µM | 30 µM |

The terminated reactions were transferred to the Caliper LabChip 3000 reader and the turnover of each reaction was measured by determining the substrate/product ratio.

Preparation of Compound Dilutions

Test compounds were dissolved in DMSO (10 mM) and transferred into 1.4 mL flatbottom or V-shaped Matrix tubes carrying a unique 2D matrix chip by individual compound hubs. The numbers of these chips were distinctively linked to the individual compound identification numbers. The stock solutions were stored at −20° C. if not used immediately. For the test procedure the vials were defrosted and identified by a scanner whereby a working sheet was generated that guided the subsequent working steps. Compound dilutions were made in 96 well plates. This format enabled the assay of maximally 40 individual test compounds at 8 concentrations (single points) including 4 reference compounds. The dilution protocol included the production of pre-dilution plates, master plates and assay plates:

Pre-dilution plates: 96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master plates: 100 µl of individual compound dilutions including standard compound and controls of the 4 "pre-dilution plates" were transferred into a 384 "master plate" including the following concentrations 1,820, 564, 182, 54.6, 18.2, 5.46, 1.82 and 0.546 µM, respectively in 90% of DMSO.

Assay plates: Identical assay plates were then prepared by pipetting 100 nL of compound dilutions of the master plates into 384-well "assay plates". In the following the compounds were mixed with 9 µl of assays components plus 9 µl enzyme corresponding to a 1:181 dilution steps enabling the final concentration of 10, 3.0, 1.0, 0.3, 0.1, 0.03, 0.01 and 0.003 µM, respectively. The preparation of the master plates were handled by the Matrix PlateMate Plus robot and replication of assay plates by the HummingBird robot.

On the basis of this study, a compound of the invention shows therapeutic efficacy especially against disorder dependant on protein kinase, especially proliferative diseases mediated by JAK/TYK kinase activity.

| Ex. No. | JAK1/IC50 (µM) | JAK3/IC50 (µM) | TYK2/IC50 (µM) |
|---|---|---|---|
| 1 | 0.838 | 7.928 | 5.513 |
| 2 | 0.582 | 1.886 | 4.593 |
| 3 | >10 | >10 | >10 |
| 4 | >10 | >10 | >10 |
| 5 | >10 | >10 | >10 |
| 6 | >10 | >10 | >10 |
| 7 | >10 | >10 | >10 |
| 8 | >10 | >10 | >10 |
| 9 | >10 | >10 | >10 |
| 10 | >10 | >10 | >10 |
| 11 | >10 | >10 | >10 |
| 12 | >10 | >10 | >10 |
| 13 | 2 | >10 | 6 |
| 14 | >10 | >10 | >10 |
| 15 | >10 | >10 | >10 |
| 16 | >10 | >10 | >10 |
| 17 | >10 | >10 | >10 |
| 18 | 0.021 | 1.2 | 0.39 |
| 19 | >10 | >10 | >10 |
| 20 | >10 | >10 | >10 |
| 21 | >10 | >10 | >10 |
| 22 | 0.01 | 0.26 | 0.13 |
| 23 | >10 | >10 | >10 |
| 24 | 0.93 | >10 | 8.5 |
| 25 | 0.071 | 3.6 | 1.1 |
| 26 | 0.034 | 3 | 0.84 |
| 27 | 1.8 | >10 | 7.8 |
| 28 | 0.55 | >10 | 3.2 |

The invention claimed is:

1. A compound of formula

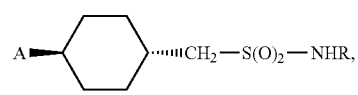

(1)

wherein
R is $C_1$-$C_4$-alkyl or $C_3$-$C_5$-cycloalkyl; and
A is a radical of formula

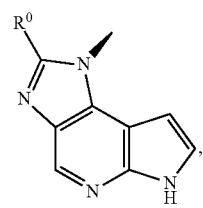

(2a')

wherein $R^0$ is H, $C_1$-$C_4$-alkyl, hydroxy-$C_1$-$C_4$-alkyl, $C_1$-$C_4$-alkoxy-$C_1$-$C_4$-alkyl or $NH_2$;
or a veterinary acceptable salt thereof.

2. The compound of claim 1 which is 1-[trans-4-((2-amino)imidazo[4,5-d]pyrrolo[2,3-b]pyridin-1(6H)-yl)cyclohexyl]-N-methylmethanesulfonamide and can be structurally represented as

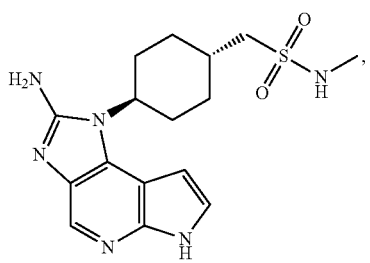 [SMILES: CNS(=O)(=O)C[C@H]1CC[C@H](n2c(N)nc3cnc4[nH]ccc4c32)CC1]

or a veterinary acceptable salt thereof.

3. A pharmaceutical composition comprising a compound according to claim 1 or a veterinary acceptable salt thereof, and a pharmaceutical acceptable carrier.

4. A method of treating atopic dermatitis, eczema, psoriasis, scleroderma, pruritus and other pruritic conditions, or allergic dermatitis, the method comprising administering to a mammal in need thereof an effective amount of a compound according to claim 1 or a veterinary acceptable salt thereof.

5. The method according to claim 4, wherein the mammal is a dog.

* * * * *